United States Patent
Hirano et al.

(10) Patent No.: US 11,610,699 B2
(45) Date of Patent: Mar. 21, 2023

(54) MULTI-CORE CABLE AND SIGNAL TRANSMISSION PATH

(71) Applicant: Hitachi Metals, Ltd., Tokyo (JP)

(72) Inventors: Koki Hirano, Tokyo (JP); Kazunori Sasaya, Tokyo (JP); Takenori Taki, Tokyo (JP); Hidetoshi Kiyohara, Hitachi (JP); Masaki Kimura, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 17/486,509

(22) Filed: Sep. 27, 2021

(65) Prior Publication Data

US 2022/0102021 A1  Mar. 31, 2022

(30) Foreign Application Priority Data

Sep. 30, 2020  (JP) .............................. JP2020-166007

(51) Int. Cl.
*H01B 7/00* (2006.01)
*H01B 7/08* (2006.01)
(Continued)

(52) U.S. Cl.
CPC ........ *H01B 7/0009* (2013.01); *A61B 1/00114* (2013.01); *H01B 7/0823* (2013.01); *H01B 7/36* (2013.01); *H01B 11/203* (2013.01)

(58) Field of Classification Search
CPC ........ H01B 11/00; H01B 7/0823; H01B 7/08; H01B 11/18; H01B 11/20; H01B 11/1813;
(Continued)

(56) References Cited

U.S. PATENT DOCUMENTS

| 46,613 A | * | 2/1865 | Southworth | ......... H01B 7/0823 |
| | | | | 160/332 |
| 327,459 A | * | 9/1885 | Spalding | .............. H01B 7/0869 |
| | | | | 174/105 R |

(Continued)

FOREIGN PATENT DOCUMENTS

| CH | 450569 A | * | 1/1966 | ............... H01B 5/18 |
| CN | 204166987 U | * | 2/2015 | ............. H01B 11/20 |

(Continued)

OTHER PUBLICATIONS

Japanese Office Action, dated Oct. 19, 2021, in Japanese Application No. 2020-166007 and English Translation thereof.

*Primary Examiner* — Krystal Robinson
(74) *Attorney, Agent, or Firm* — McGinn I.P. Law Group, PLLC

(57) ABSTRACT

A multi-core cable includes a plurality of coaxial cables being arranged in parallel with each other, and a synthetic resin covering member that collectively covers the plurality of coaxial cables. Each coaxial cable includes a center conductor, an insulator covering an outer periphery of the center conductor, and a metal outer conductor covering an outer periphery of the insulator. The covering member holds the plurality of coaxial cables in such a manner that the plurality of coaxial cables are aligned side by side along a direction perpendicular to a longitudinal direction of the plurality of coaxial cables. At least a part of the outer conductors of the plurality of the coaxial cables respectively contacts the covering member.

20 Claims, 8 Drawing Sheets

(51) Int. Cl.
*A61B 1/00* (2006.01)
*H01B 11/20* (2006.01)
*H01B 7/36* (2006.01)

(58) Field of Classification Search
CPC .............. H01B 13/067; H01B 13/0162; H01B 7/0216; H01B 11/1821; H01B 13/06; H01B 13/2626; H01B 7/184; H01B 7/0009; H01R 13/6658
USPC ........................................................ 174/103
See application file for complete search history.

(56) References Cited

U.S. PATENT DOCUMENTS

| | | | | |
|---|---|---|---|---|
| 352,771 | A * | 11/1886 | Morehouse | H01B 7/202 174/102 C |
| 681,470 | A * | 8/1901 | Wolff | H01B 7/0823 174/136 |
| 1,370,731 | A * | 3/1921 | Chase | H01B 9/023 174/103 |
| 2,123,746 | A * | 7/1938 | Rost | H01B 7/0208 428/397 |
| 2,203,232 | A * | 6/1940 | Osborne | H01B 7/2806 74/108 |
| 2,377,153 | A * | 5/1945 | Vassar | H01B 9/02 174/106 SC |
| 2,628,998 | A * | 2/1953 | Frisbie | H01B 7/0823 425/114 |
| 2,966,644 | A * | 12/1960 | Hafner | H01P 3/08 174/128.1 |
| 2,981,788 | A * | 4/1961 | Bunish | H01B 9/028 174/103 |
| 3,600,500 | A * | 8/1971 | Schoerner | H01B 7/182 174/115 |
| 3,663,739 | A * | 5/1972 | Chevrier | H01B 7/08 174/32 |
| 3,775,552 | A * | 11/1973 | Schumacher | H01B 7/0838 174/105 R |
| 3,936,591 | A * | 2/1976 | Smith | H01B 7/185 174/115 |
| 3,984,653 | A * | 10/1976 | Blaas | B23K 9/1081 219/136 |
| 4,012,577 | A * | 3/1977 | Lang | H01B 7/0876 174/34 |
| 4,227,041 | A * | 10/1980 | Den | H01B 7/04 174/117 F |
| 4,281,212 | A * | 7/1981 | Bogese, II | H01B 7/0823 174/103 |
| 4,284,841 | A * | 8/1981 | Tijunelis | H01B 7/046 174/11 ON |
| 4,314,737 | A * | 2/1982 | Bogese | H01R 12/775 174/106 SC |
| 4,404,424 | A * | 9/1983 | King | H01B 7/0876 174/32 |
| 4,449,013 | A * | 5/1984 | Garshick | H01B 7/226 174/109 |
| 4,600,805 | A * | 7/1986 | Glynn | H01B 7/08 174/102 R |
| 4,638,117 | A * | 1/1987 | Ney | H01B 7/38 174/115 |
| 4,674,822 | A * | 6/1987 | Hall | H01R 4/2404 439/399 |
| 4,749,823 | A * | 6/1988 | Ziemek | B21D 15/04 174/109 |
| 5,384,430 | A * | 1/1995 | Anthony | H01B 7/046 174/102 R |
| 5,668,912 | A * | 9/1997 | Keller | G02B 6/4416 385/100 |
| 5,973,268 | A * | 10/1999 | Cheng | H01B 7/361 174/117 F |
| 6,259,019 | B1 * | 7/2001 | Damilo | H01B 13/262 174/105 R |
| 7,880,089 | B1 * | 2/2011 | Herrin | H01B 9/028 174/113 R |
| 7,956,290 | B2 * | 6/2011 | Wang | H01B 11/00 174/117 F |
| 8,124,875 | B2 * | 2/2012 | Aitken | H01B 9/028 174/109 |
| 8,169,794 | B2 * | 5/2012 | Matsukawa | H04M 1/0237 174/117 FF |
| 8,487,186 | B2 * | 7/2013 | Walid | H01B 7/0869 174/117 F |
| 8,598,461 | B2 * | 12/2013 | Lind | H02G 3/32 174/72 A |
| 8,664,817 | B2 * | 3/2014 | Rumbaugh | H02K 3/30 310/87 |
| 10,147,523 | B2 * | 12/2018 | Rengert | H01B 11/1091 |
| 10,784,022 | B1 * | 9/2020 | Lee | H01B 7/02 |
| 2007/0068696 | A1 * | 3/2007 | Matsui | H01B 11/1025 174/113 R |
| 2008/0035367 | A1 * | 2/2008 | Tanaka | H01B 11/1804 174/102 R |
| 2013/0153260 | A1 * | 6/2013 | Favereau | H01B 3/441 174/102 C |
| 2017/0162301 | A1 * | 6/2017 | Chen | H01B 7/0216 |
| 2019/0296465 | A1 | 9/2019 | Vana, Jr. et al. | |

FOREIGN PATENT DOCUMENTS

| | | | | |
|---|---|---|---|---|
| CN | 105609178 | A | * 5/2016 | |
| CN | 113838612 | A | * 12/2021 | ......... H01B 11/1821 |
| GB | 1371211 | A | * 10/1974 | ........... H01B 7/0823 |
| JP | S48-44474 | U | 6/1973 | |
| JP | S56-169315 | U | 12/1981 | |
| JP | H02-142019 | A | 5/1990 | |
| JP | H09-237523 | A | 9/1997 | |
| JP | 2006-252898 | A | 9/2006 | |
| JP | 2009-211855 | A | 9/2009 | |
| JP | 2010-097773 | A | 4/2010 | |
| JP | 2019-525411 | A | 9/2019 | |

* cited by examiner

MULTI-CORE CABLE AND SIGNAL TRANSMISSION PATH

CROSS-REFERENCES TO RELATED APPLICATION

The present application is based on Japanese patent application No. 2020-166007 filed on Sep. 30, 2020, and the entire contents of which are incorporated herein by reference.

BACKGROUND OF THE INVENTION

1. Field of the Invention

The present invention relates to a multi-core cable including a plurality of coaxial cables and a signal transmission path including the multi-core cable and a substrate.

2. Description of the Related Art

Conventionally, for example, an endoscope system, in which a flat cable is used as an assembled (aggregated) cable for connecting a camera head configured to be inserted into a body of a patient (subject) and a main device configured to be arranged outside the body of the patient (subject) and comprising a signal processing circuit or the like for processing an image signal output from the camera head, has been known (see e.g., JP2010-097773A).

The flat cable described in JP2010-097773A comprises a flat cable core formed by arranging a plurality of coaxial cables in substantially parallel to each other in one line, and a sheath layer formed by covering substantially an entire outer periphery of the flat cable core with a synthetic resin as a covering member. The sheath layer is formed in a flat tube shape by extrusion molding the synthetic resin and serves as a binding layer for binding the plurality of coaxial cables. Each coaxial cable comprises a center conductor, an inner insulating layer provided at an outer periphery of the center conductor, an outer conductor provided at an outer periphery of the inner insulating layer, and a jacket as an outer insulating layer provided at an outer periphery of the outer conductor. At an end of the flat cable, the coaxial cables are led from the sheath layer, and the center conductors of the coaxial cables are connected to a connection terminal on a printed circuit board. Further, the outer conductors are often individually or collectively connected to the connection terminal.

JP2009-211855A describes a flat cable including a plurality of coaxial cables arranged side by side in parallel. In this flat cable, the plurality of coaxial cables are collectively covered with a collective outer sheath composed of a resin. Each coaxial cable comprises a center conductor composed of a stranded wire, an insulator covering an outer periphery of the center conductor, an outer conductor being laterally wrapped around an outer periphery of the insulator, and an outer sheath being composed of a resin and covering the outer conductor. The collective outer sheath is formed by extrusion molding a heated resin with the use of an extruder.

Patent Document 1: JP2010-097773A
Patent Document 2: JP2009-211855A

SUMMARY OF THE INVENTION

In the flat cable disclosed in JP2010-097773A, the jackets of the respective coaxial cables linearly contact with the sheath layer. If a binding force of the sheath layer at a contact portion is low, the coaxial cables will be separated from the sheath layer, so that the arrangement of the plurality of coaxial cables inside the sheath layer is disordered. In the meantime, if the binding force of the sheath layer at the contact part is high, it will be hard to strip off an end of the sheath layer to expose the coaxial cables in terminal processing of the flat cable. Similarly, in the flat cable disclosed in JP2009-211855A, if the collective outer sheath is welded with outer sheaths of the respective coaxial cables when the collective sheath is formed by extrusion molding, it will be hard to strip off an end of the collective outer sheath in a longitudinal direction of the flat cable to expose the coaxial cables.

Thus, it is an object of the invention to provide a multi-core cable for which terminal processing can be easily performed, and a signal transmission path comprising the multi-core cable.

According to one aspect of the present invention, a multi-core cable, comprises:
a plurality of coaxial cables being arranged in parallel with each other; and
a covering member comprising a synthetic resin and collectively covering the plurality of coaxial cables,
wherein each of the plurality of coaxial cables comprises a center conductor, an insulator covering an outer periphery of the center conductor, and an outer conductor comprising a metal and covering an outer periphery of the insulator,
wherein the covering member is configured to hold the plurality of coaxial cables in such a manner that the plurality of coaxial cables are aligned side by side along a direction perpendicular to a longitudinal direction of the plurality of coaxial cables,
wherein at least a part of respective outer conductors of the plurality of the coaxial cables contacts the covering member.

Further, according to another aspect of the present invention, a signal transmission path, comprises:
the multi-core cable as described above; and
a substrate comprising a plurality of wires including pads configured to be connected to the center conductors of the plurality of coaxial cables,
wherein a pitch between the center conductors is equal to a pitch between the pads of the substrate in an alignment direction of the plurality of coaxial cables.

Advantageous Effects of Invention

According to the present invention, it is possible to provide a multi-core cable for which a terminal processing can be easily performed, and a signal transmission path comprising the multi-core cable.

BRIEF DESCRIPTION OF THE DRAWINGS

Next, preferred embodiments according to the present invention will be described with reference to appended drawings, wherein.

DETAILED DESCRIPTION OF THE PREFERRED EMBODIMENTS

First Embodiment

Figure 1:
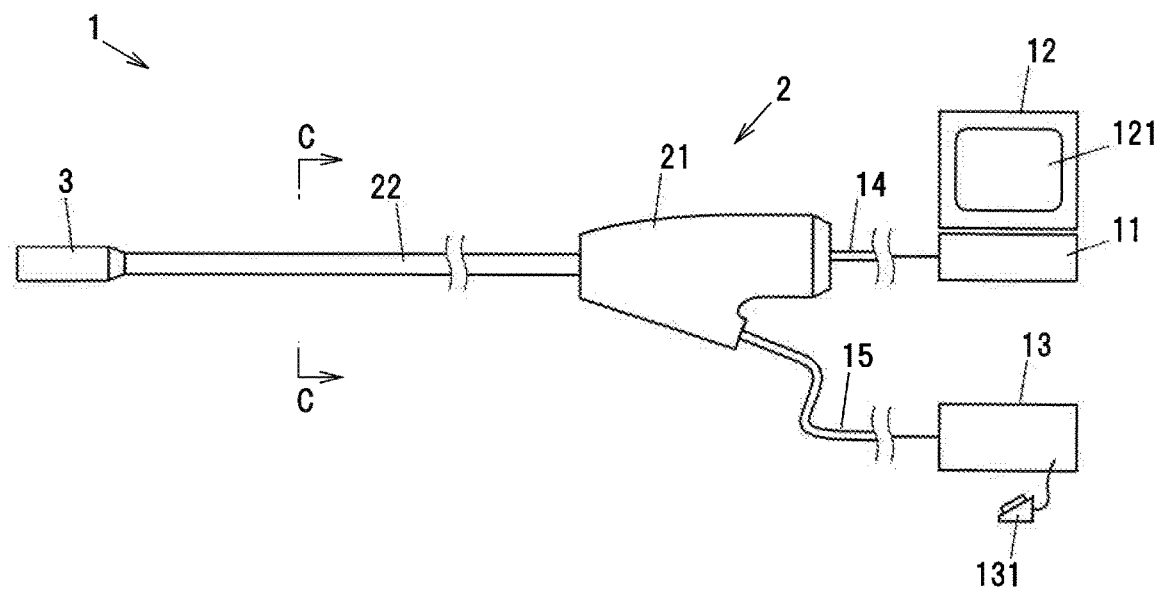
FIG. 1 is a schematic diagram showing an example of a schematic configuration of an endoscope system comprising a multi-core cable and a signal transmission path according to the first embodiment of the present invention.

FIG. 1 is a schematic diagram showing an example of a schematic configuration of an endoscope system 1 comprising a multi-core cable and a signal transmission path according to the first embodiment of the present invention. The endoscope system 1 comprises an endoscope 2, an image processing device 11 for processing an image data obtained by the endoscope 2, a display device 12 for displaying an image processed by the image processing device 11 on a screen 121, and a liquid supply device 13 for ejecting liquid such as physiological saline solution in accordance with an operation of a foot switch 131.

The endoscope 2 comprises an operational unit 21 configured to be operated by an endoscopy engineer, an insertion tube 22 extending from the operational unit 21, and a camera head 3 attached at a tip end of the insertion tube 22. The operational unit 21 is connected to the image processing device 11 via a communication cable 14, and is connected to the liquid supply device 13 via a hose 15. The camera head 3 is inserted together with a part of the insertion tube 22 into a body of a patient (subject). A length of the insertion tube 22 is, e.g., 1 to 4 m.

Figure 2A:
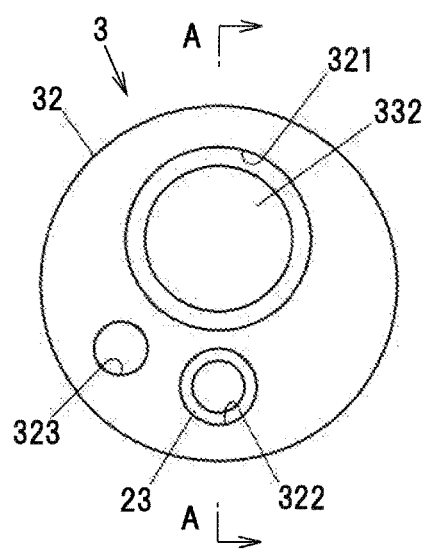
FIG. 2A is an end surface view showing an end surface of a camera head.
Figure 2B:
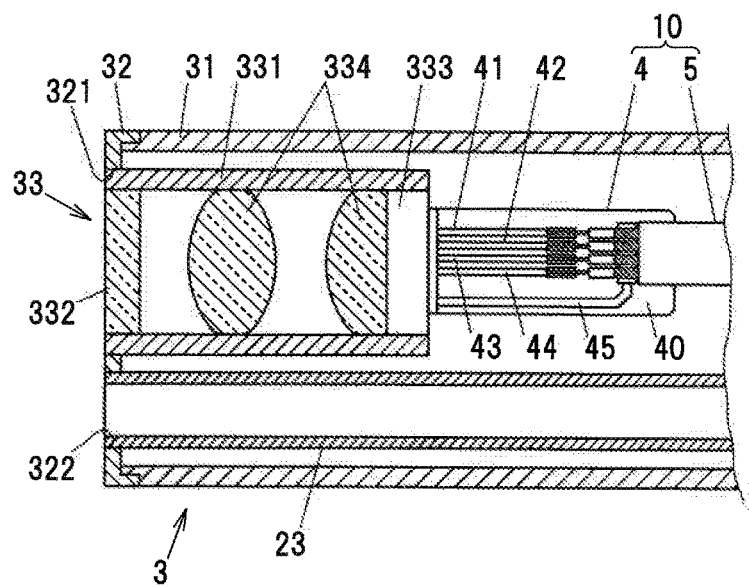
FIG. 2B is a cross-sectional view showing a configuration example of an inside of the camera head in FIG. 2A cut along a line A-A.

FIG. 2A is an end surface view showing an end surface of the camera head 3. FIG. 2B is a cross-sectional view showing a configuration example of an inside of the camera head 3 in FIG. 2A cut along a line A-A. The camera head 3 comprises an outer cylindrical member 31 composed of a rigid resin, a cover member 32 for closing (plugging) a tip end surface of the outer cylindrical member 31, and an imaging unit 33. The outer cylindrical member 31 and the insertion tube 22 are configured to accommodate a tube 23 for guiding the liquid supplied from the liquid supply device 13 to an imaging target region of the imaging unit 33 and a signal transmission path 10 to be described later.

The cover member 32 includes a first through-hole 321 into which the imaging unit 33 is fitted and a second through-hole 322 into which a tip end of the tube 23 is fitted. The cover member 32 further includes an irradiation window 323 for emitting an irradiation light to irradiate the imaging target region. The light led by an optical fiber (to be described later) housed in the insertion tube 22 is irradiated from the irradiation window 323.

The imaging unit 33 includes a cylindrical member 331 composed of a metal, a light-transmissive window 332 fixed at one end of the cylindrical member 331, an imaging element 333 fixed at the one end of the cylindrical member 331, and a plurality of lenses 334 arranged between the window 332 and the imaging element 333. The imaging element 333 is, e.g., a charge-coupled device (CCD) image sensor, or a Complementary MOS (CMOS) image sensor. The imaging unit 33 is configured to convert an image data imaged in the imaging element 333 into an electric signal and output the electric signal.

The electric signal output from the imaging unit 33 is transmitted to the image processing device 11 through the operational unit 21 via the signal transmission path 10 of the endoscope 2. The signal transmission path 10 comprises a substrate 4 being housed in the outer cylindrical member 31, and a multi-core cable 5 being connected to the substrate 4 at one end and being housed in the insertion tube 22. The signal transmission path 10 is configured to transmit the electric signal output from the imaging unit 33 and supply an electric power to the imaging element 333. The substrate 4 is a flexible substrate (Flexible Printed Circuits: FPC) or a printed substrate (Printed Circuit Board: PCB). First to fifth wires 41 to 45 composed of an electrically conductive metal such as a copper film are formed on a front surface of a base 40 composed of an electrically insulative resin. Further, the wires of the flexible substrate or the printed substrate may be arranged at an inner layer or a bottom surface of the base 40.

Figure 3A:
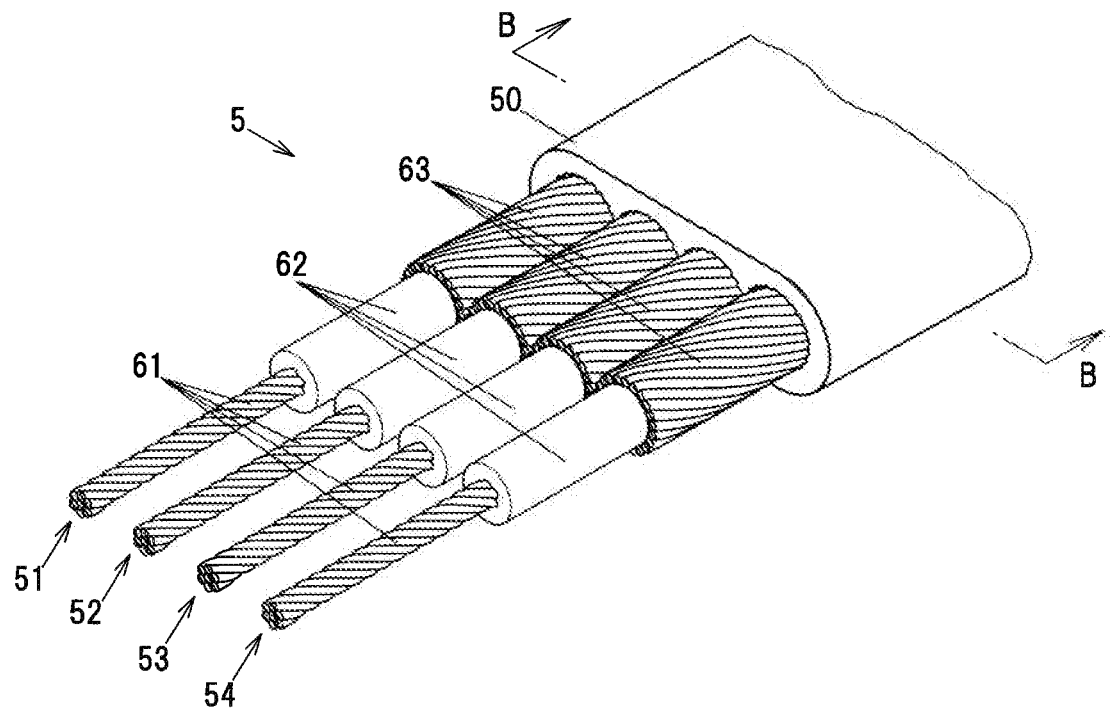
FIG. 3A is a perspective view showing an end of the multi-core cable.
Figure 3B:
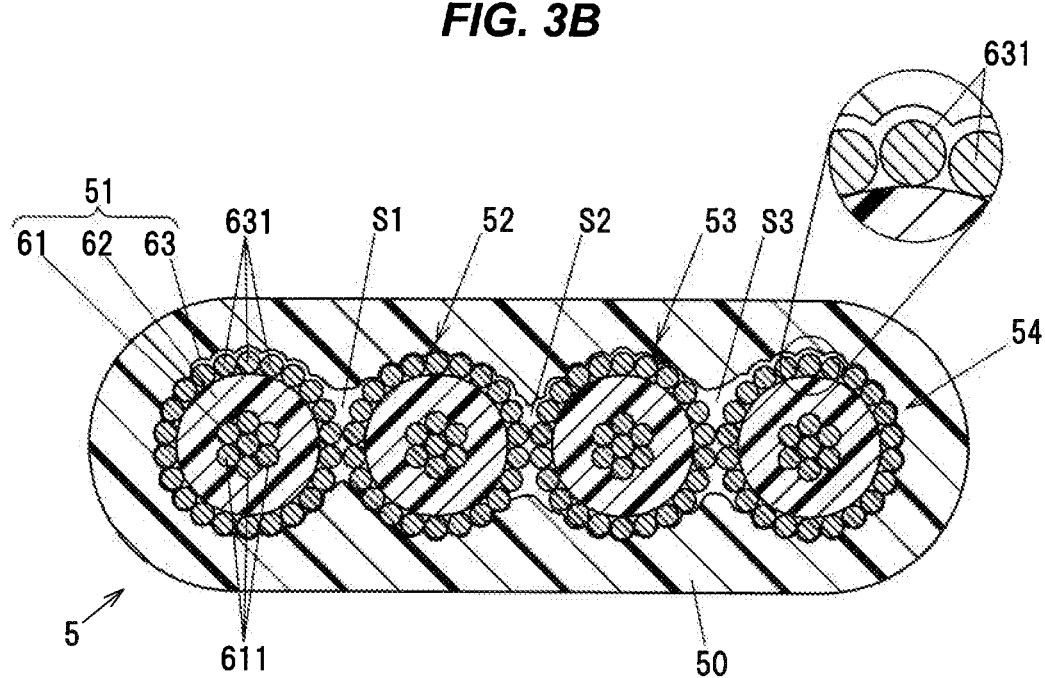
FIG. 3B is a cross-sectional view of the multi-core cable in FIG. 3A cut along a line B-B of FIG. 3A.

FIG. 3A is a perspective view showing an end of the multi-core cable 5. FIG. 3B is a cross-sectional view of the multi-core cable 5 in FIG. 3A cut along a line B-B of FIG. 3A. The multi-core cable 5 is a flat cable comprising a covering member 50 composed of a synthetic resin and a plurality of coaxial cables 51 to 54 being arranged side by side in parallel with each other. The plurality of coaxial cables 51 to 54 are collectively covered with the covering member 50. The covering member 50 is configured to hold the plurality of coaxial cables 51 to 54 in such a manner that the plurality of coaxial cables 51 to 54 are aligned (arranged in one line) along a direction perpendicular to longitudinal directions of the respective coaxial cables 51 to 54. Hereinafter, the plurality of coaxial cables 51 to 54 will be explained as the first to fourth coaxial cables 51 to 54 in accordance with the arrangement order.

Each of the first to fourth coaxial cables 51 to 54 comprises a center conductor 61, an insulator 62 covering an outer periphery of the center conductor 61, and an outer conductor 63 covering an outer periphery of the insulator 62. Each of the center conductor 61 and the outer conductor 63 is composed of a metal with good electrical conductivity such as copper. In the present embodiment, although the center conductor 61 of each of the first to fourth coaxial cables 51 to 54 is composed of a stranded wire produced by stranding a plurality of wires 611, the present invention is not limited thereto. The center conductor 61 may be composed of a single wire. Further, the center conductor 61 of some of the first to fourth coaxial cables 51 to 54 may be composed of the stranded wire and the center conductor 61 of the others of the first to fourth coaxial cables 51 to 54 may be composed of the single wire. A thickness of the center conductor 61 is, e.g., 36 American Wire Gauge (AWG) or more, and 52 AWG or less.

The outer conductor 63 of each of the first to fourth coaxial cables 51 to 54 is configured by helically and laterally winding the plurality of wires 631 in such a manner as to contact an outer peripheral surface of the insulator 62. The outer conductor 63 may not be composed of the plurality of wires 631 but have a foil structure produced by plating. The outer conductor 63 may be configured by longitudinally lapping or laterally winding an electrically conductive tape including a tape member composed of a resin and conductor wires formed on one surface of the tape member around the insulator 62. A part of the outer peripheral surface of the outer conductor 63 of each of the first to fourth coaxial cables 51 to 54 contacts the covering member 50.

The outer conductors 63 of each of the first to fourth coaxial cables 51 to 54 is not covered with the outer sheath, e.g., as shown in the coaxial cable described in JP 2009-211855 A, but directly covered with the covering member 50. Hereby, a width of the multi-core cable 5 along an alignment direction of the first to fourth coaxial cables 51 to 54 decreases, and a thickness of the multi-core cable 5 in a direction perpendicular to the alignment direction of the multi-core cable 5 and the longitudinal directions of the first to fourth coaxial cables 51 to 54 decreases. The width of the multi-core cable 5 is, e.g., 0.5 mm or more and less than 2 mm. The thickness of the multi-core cable 5 is, e.g., 0.25 mm or more and less than 0.5 mm. Hereinafter, the alignment direction of the first to fourth coaxial cables 51 to 54 of the multi-core cable 5 will be referred to as "width direction". Since the outer conductor 63 of each of the coaxial cables 51 to 54 is not covered with the outer sheath (jacket), e.g., as described in the Patent Documents 1 and 2, a step of stripping off the outer sheath before performing solder connection can be omitted.

As shown in FIG. 3B, in any cross-section of the multi-core cable 5 in a direction perpendicular to the longitudinal direction of the first to fourth coaxial cables 51 to 54, a gap (space) is formed between the covering member 50 and at least a part of outer peripheries of the outer conductors 63 of the first to fourth coaxial cables 51 to 54. In FIG. 3B, a gap between the outer conductors 63, 63 of the first and second coaxial cables 51, 52 and the covering member 50, a gap between the outer conductors 63, 63 of the second and third coaxial cables 52, 53 and the covering member 50, and a space between the outer conductors 63, 63 of the third and fourth coaxial cables 53, 54 and the covering member 50 are respectively shown as S1, S2, and S3. In other words, regions where the covering member 50 is not interposed between the respective outer conductors 63 of the first to fourth coaxial cables 51 to 54 exists in the width direction of the multi-core cable 5. Further, as shown in an enlarged view in FIG. 3B, the gap between the outer conductor 63 and the covering member 50 may be formed at a region other than the regions between the first to fourth coaxial cables 51 to 54 in the width direction of the multi-core cable 5.

The center conductors 61 of the first to fourth coaxial cables 51 to 54 are arranged at equal intervals in the width direction of the multi-core cable 5. The outer conductors 63 of the first to fourth coaxial cables 51 to 54 contact with each other at least in a part of the longitudinal direction of the multi-core cable 5. The outer conductors 63 have the same potentials and are electrically grounded as the ground for a power source of the imaging element 333 and a reference potential of the electric signal output from the imaging element 333.

The covering member 50 is formed by extruding a melted resin by an extruder to surround the first to fourth coaxial cables 51 to 54, and then reducing (drawing) the extruded resin to be pressed against the outer conductors 63 of the first to fourth coaxial cables 51 to 54 in the width direction and the thickness direction, and then cool curing in this state. In the present embodiment, the covering member 50 is composed of a fluororesin, and shapes of the wires 631 of the outer conductor 63 are transferred to an inner surface of the covering member 50 in a part where the melted resin contacts the wires 631 of the outer conductor 63 in the reducing process. Meanwhile, the wires 631 are not fixed at the covering member 50, so that the covering member 50 can be easily separated from the outer conductor 63. Further, the contact between the melted resin and the insulator 62 when molding the covering member 50 is blocked by the outer conductor 63. Hereby, the covering member 50 does not contact with the insulator 62. The material of the covering member 50 is not limited to the fluororesin, and may be resins such as polyethylene, polypropylene, vinyl chloride (chloroethylene), and urethane.

Figure 4:
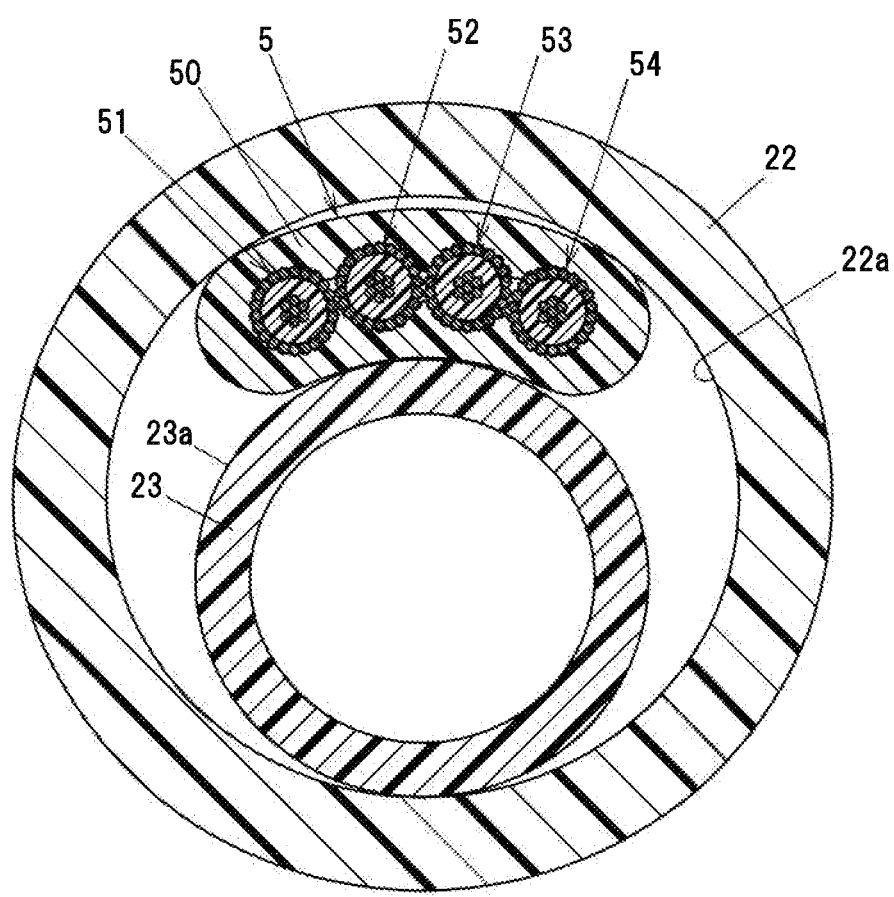
FIG. 4 is a cross-sectional view showing an insertion tube in FIG. 1 cut along a line C-C.

FIG. 4 is a cross-sectional view showing an insertion tube 22 in FIG. 1 cut along a line C-C. The insertion tube 22 houses the multi-core cable 5 and the tube 23. Further, in the insertion tube 22, a plurality of optical fibers 80 for guiding a light irradiated from the irradiation window 323 to the camera head 3 and a banding tube 81 for banding and housing the plurality of optical fibers 80 are arranged.

Each of the insertion tube 22 and the tube 23 has a circular cross-section. The multi-core cable 5 is arranged between an inner peripheral surface 22a of the insertion tube 22 and an outer peripheral surface 23a of the tube 23. In the cross-section shown in FIG. 4, both ends of the covering member 50 in the width direction of the multi-core cable 5 abut on the inner peripheral surface 22a of the insertion tube 22, a center part of the covering member 50 in the width direction of the multi-core cable 5 abuts on the outer peripheral surface 23a of the tube 23, and the multi-core cable 5 elastically deforms in a circular-arc shape. Further, one or more notches may be provided at an opposite surface of the covering member 50 to the inner peripheral surface 22a of the insertion tube 22 in such a manner that the multi-core cable 5 easily deforms into the circular-arc shape.

A difference between an outer diameter of the tube 23 and an inner diameter of the insertion tube 22 is set to be slightly greater than the thickness of the multi-core cable 5. Since the multi-core cable 5 deforms into the circular-arc shape, it is possible to arrange the multi-core cable 5 between the inner peripheral surface 22a and the outer peripheral surface 23a of the tube 23, even though the difference between the outer diameter of the tube 23 and the inner diameter of the insertion tube 22 is set to be slightly greater than the thickness of the multi-core cable 5.

The multi-core cable 5 is connected to the substrate 4 after being processed with a predetermined terminal processing. In the terminal processing, as shown in FIG. 3A, a processing for sequentially pulling out the outer conductors 63, the insulators 62, and the center conductors 6 of the respective first to fourth coaxial cables 51 to 54 from the covering member 50 is performed. Thereafter, the outer conductors 63 and the center conductors 61 are soldered at pads (to be described later) on the substrate 4. In the meantime, it is preferable that colors of the insulators 62 are different from each other in the first to fourth coaxial cables 51 to 54 in order to prevent the misconnection. Next, a method for performing the above processing by using a laser beam will be explained in conjunction with FIG. 5.

Figure 5A:
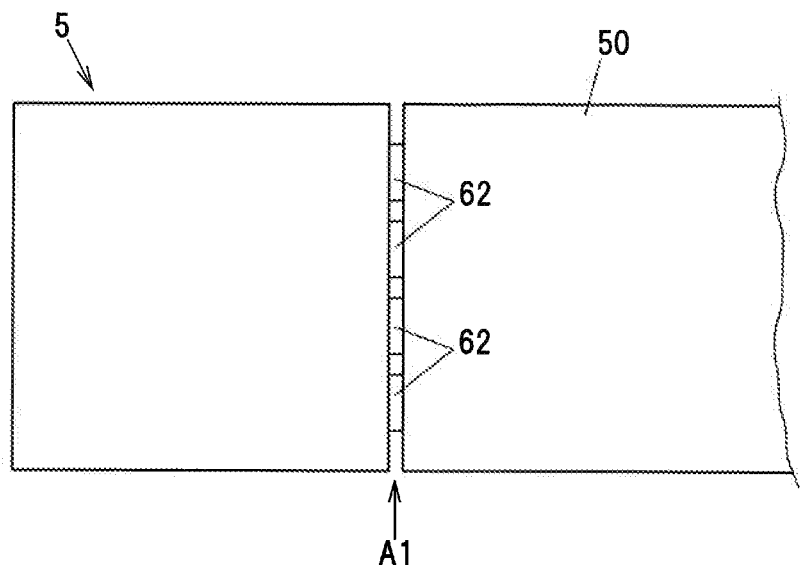
FIGS. 5A to 5C are explanatory diagrams showing each step of processing for respectively deriving outer conductors, insulators, and center conductors of first to fourth coaxial cables from a covering member.
Figure 5B:
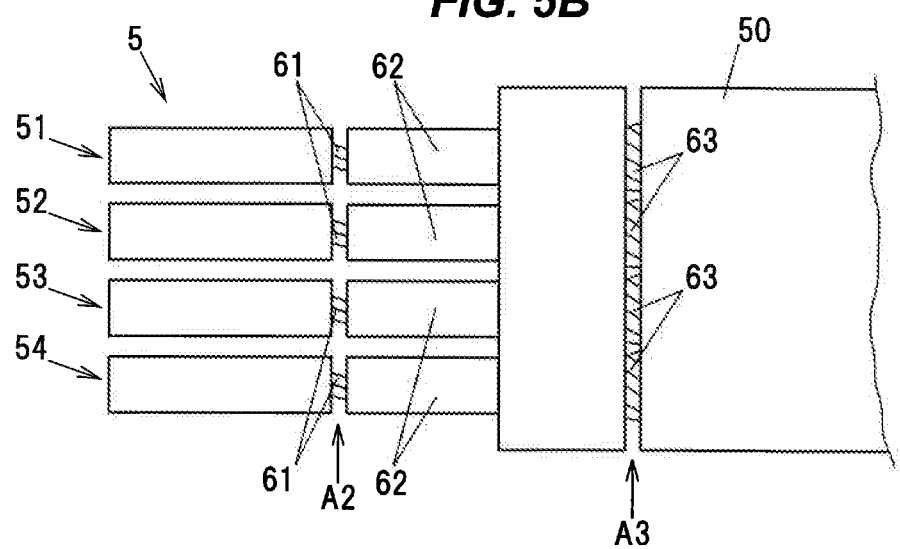
Figure 5C:
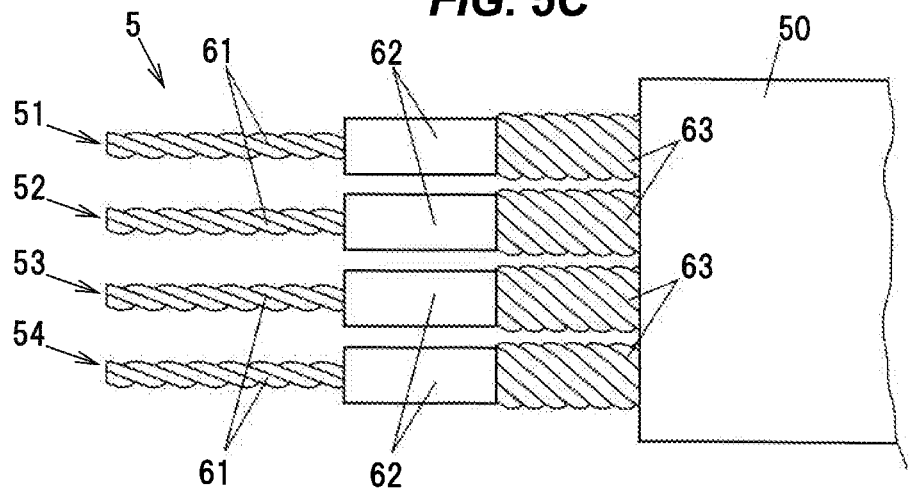

FIGS. 5A to 5C are explanatory diagrams showing each step of processing for respectively deriving the outer conductors 63, the insulators 62, and the center conductors 61 of the first to fourth coaxial cables 51 to 54 from the covering member 50. FIG. 5A shows the state where the covering member 50 and the outer conductor 63 are linearly cut along the width direction of the multi-core cable 5 by irradiating a laser beam to a position indicated by an arrow A1 in the longitudinal direction of the multi-core cable 5. A part of the covering member 50 and a part of the outer conductors 63 on a tip end side (on a side closer to the tip end) of the multi-core cable 5 with respect to the position indicated by the arrow A1 (left side in FIG. 5A) are removed by being pulled out in the longitudinal direction of the multi-core cable 5. In the meantime, it is preferable that each of the coaxial cables 51 to 54 has the same structure except the color of the insulator 62 in terms of the workability in cutting the coating members by the laser beam irradiation.

FIG. 5B shows the state where the insulators 62 of the first to fourth coaxial cables 51 to 54 are cut by irradiating a laser beam to a position indicated by an arrow A2 in the longitudinal direction of the multi-core cable 5, and the covering member 50 is cut by irradiating a laser beam to a position indicated by an arrow A3 in the longitudinal direction of the multi-core cable 5. FIG. 5C shows the state where a part of the insulators 62 on the tip end side of the multi-core cable 5 with respect to the position indicated by the arrow A2 and a part of the covering member 50 on the tip end side of the multi-core cable 5 with respect to the position indicated by the arrow A3 are removed by being pulled out in the longitudinal direction of the multi-core cable 5. The multi-core cable 5 is connected to the substrate 4 with being terminal processed as described above.

Figure 6A:
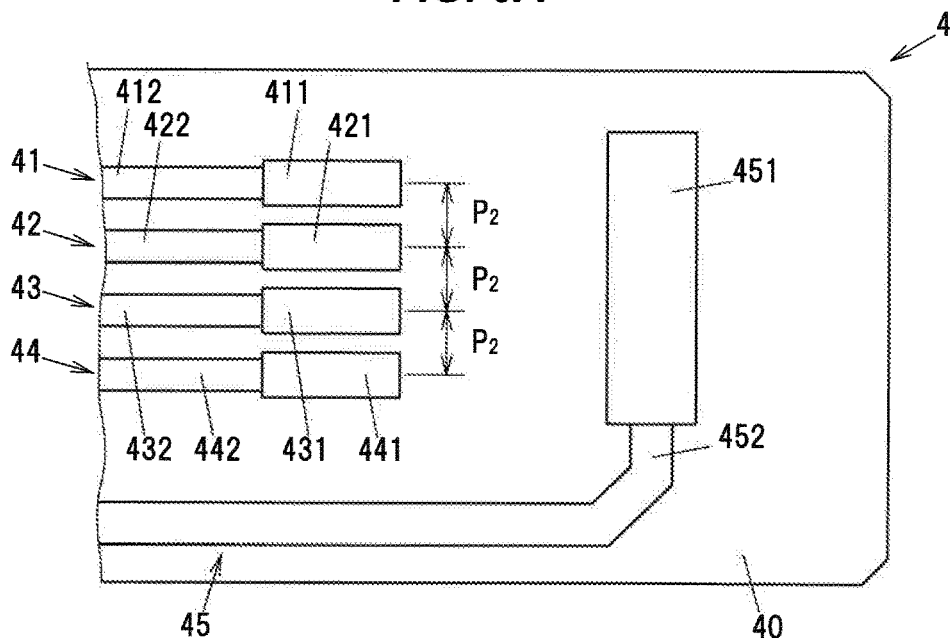
FIG. 6A is a plan view showing a connecting portion of the multi-core cable on a substrate.

FIG. 6A is a plan view showing a connecting portion of the multi-core cable 5 on the substrate 4. In the substrate 4, first to fourth wires 41 to 44 configured to be electrically connected to the center conductors 61 of the first to fourth coaxial cables 51 to 54 respectively and a fifth wire 45 configured to be electrically connected to the outer conductors 63 of the first to fourth coaxial cables 51 to 54 together are formed on the front surface of the base 40. However, the first to fifth wires 41 to 45 may be formed on an inner layer or the back surface of the substrate 4, via a through-hole formed in the substrate 4. The first to fourth wires 41 to 44 respectively comprise pads 411, 421, 431, 441 configured to be connected to the center conductors 61, and transmission paths 412, 422, 432, 442 extending from the pads 411, 421, 431, 441. The fifth wire 45 comprises a pad 451 configured to be connected to the outer conductors 63 of the first to fourth coaxial cables 51 to 54, and a transmission path 452 extending from the pad 451. A resist film (not shown) is formed on the front surface of the substrate 4 except the regions where the pads 411, 421, 431, 441 are formed. However, the resist film may be omitted.

Figure 6B:
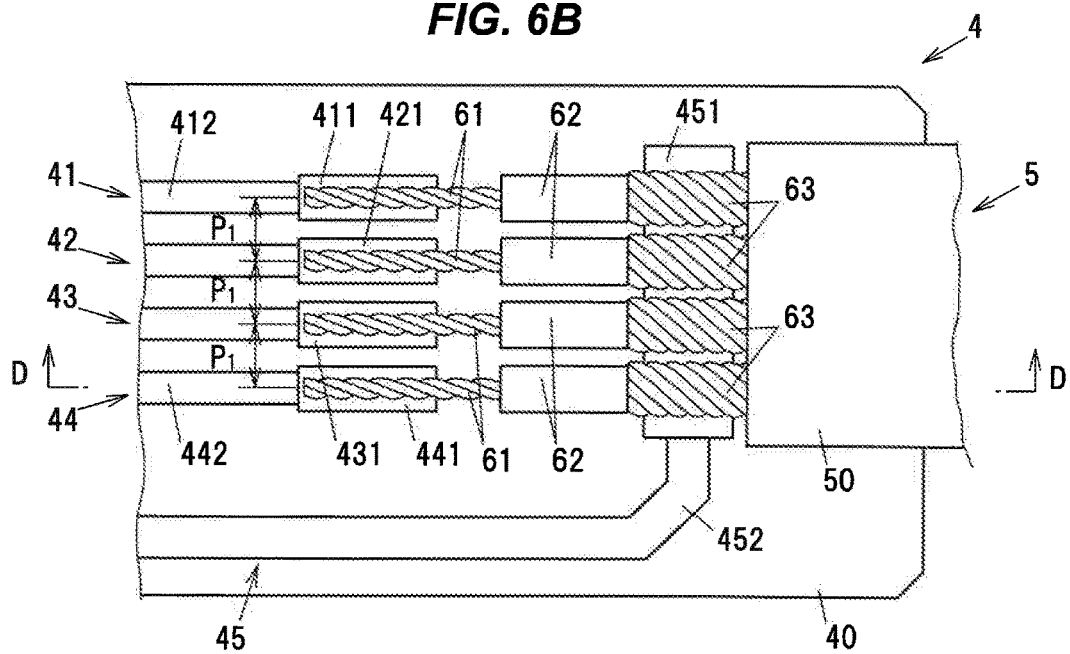
FIG. 6B is an explanatory diagram showing a state where the multi-core cable after the terminal processing is arranged on the substrate.
Figure 6C:
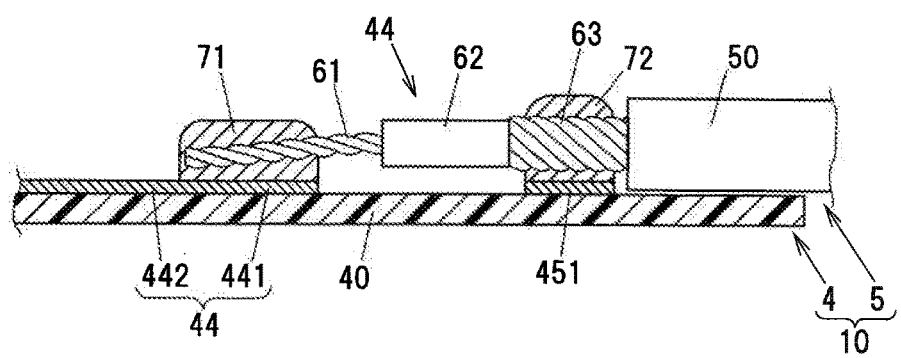
FIG. 6C is a cross-sectional view of the substrate in FIG. 6B cut along a line D-D.

FIG. 6B is an explanatory diagram showing a state where the multi-core cable 5 after the terminal processing is arranged on the substrate 4. FIG. 6C is a cross-sectional view of the substrate 4 in FIG. 6B cut along a line D-D. The center conductors 61 of the first to fourth coaxial cables 51 to 54 are respectively connected to the pads 411, 421, 431, 441 of the first to fourth wires 41 to 44 by a solder 71, and the outer conductors 63 of the first to fourth coaxial cables 51 to 54 are collectively connected to the pad 451 of the fifth wire 45 by a solder 72.

A pitch P1 between the center conductors 61 of the first to fourth coaxial cables 51 to 54 in the width direction of the multi-core cable 5 (see e.g., FIG. 6B) should be substantially equal to a pitch P2 between the pads 411, 421, 431, 441 in the same direction (see e.g., FIG. 6A). The pitch P1 is an interval between center lines of one pair of the adjacent ones in the width direction of the multi-core cable $5n$ of the center conductors 61 of the first to fourth coaxial cable 51 to 54. The pads 411, 421, 431, 441 are formed in a region where the respective center conductors 61 overlap the pads 411, 421, 431, 441 in the thickness direction of the substrate 4 when the center conductors 61 of the first to fourth coaxial cable 51 to 54 are pulled out in parallel with each other along the longitudinal direction of the multi-core cable 5.

The pad 451 of the fifth wire 45, to which the outer conductors 63 of the first to fourth coaxial cable 51 to 54 are connected, is formed in a lengthy band shape in the width direction of the multi-core cable 5. A length of the pad 451 is the same as the width of the multi-core cable 5, and the respective outer conductors 63 pulled out from the covering member 50 along the longitudinal direction of the multi-core cable 5 are formed in a region where the outer conductors 63 being in parallel with each other overlap with the pad 451 in the thickness direction of the substrate 4.

The center conductors 61 and the outer conductors 63 of the first to fourth coaxial cables 51 to 54 may be soldered by, e.g., using a laser beam or using a device having a mechanism of instantaneously heating a flat plate to heat the solder on the first to fourth coaxial cables 51 to 54.

Advantageous Effects of the First Embodiment

According to the first embodiment of the present invention, since each of the outer conductors 63 of the first to fourth coaxial cables 51 to 54 contacts the covering member 50 collectively covering the first to fourth coaxial cable 51 to 54, the outer conductors 63 can be separated easily from the covering member 50, and the terminal processing of the multi-core cable 5 can be performed easily. Further, since the gap is formed between at least a part of outer peripheries of the outer conductors 63 and the covering member 50 in the cross-section perpendicular to the longitudinal directions of the first to fourth coaxial cables 51 to 54, the covering member 50 can be separated more easily, and the terminal processing of the multi-core cable 5 can be performed more easily.

Further, since the multi-core cable 5 is not covered with an outer sheath as in the coaxial cable described in, e.g., the JP2009-211855A, and the multi-core cable 5 is directly covered with the covering member 50, the multi-core cable 5 can be reduced in size and weight. Thus, a work for removing the outer sheath can be omitted and the intervals between the respective center conductors 61 can be reduced. Therefore, it is possible to connect the multi-core cable 5 with the substrate 4 with reducing the pitch P1 between the center conductors 61 and the pitch P2 between the pads 411, 421, 431, 441.

Further, since the gap is formed between the covering member 50 and at least a part of the outer peripheries of the outer conductors 63 of the first to fourth coaxial cables 51 to 54, the covering member 50 can be separated easily from the first to fourth coaxial cables 51 to 54, and the separated first to fourth coaxial cables 51 to 54 can be maintained in a linear shape. The first to fourth coaxial cables 51 to 54 can be easily connected to the substrate 4 even though the pitch P2 is narrow.

Furthermore, in the multi-core cable 5, since the pitch P1 between the respective center conductors 61 in the alignment direction of the first to fourth coaxial cables 51 to 54 is substantially equal to the pitch P2 between the pads 411, 421, 431, 441 in the alignment direction of the pads 411, 421, 431, 441 in the substrate 4, the alignment between the respective center conductors 61 and the pads 411, 421, 431, 441 can be performed easily, and the soldering of the respective center conductors 61 to the pads 411, 421, 431, 441 can be easily conducted.

Second Embodiment

Figure 7A:
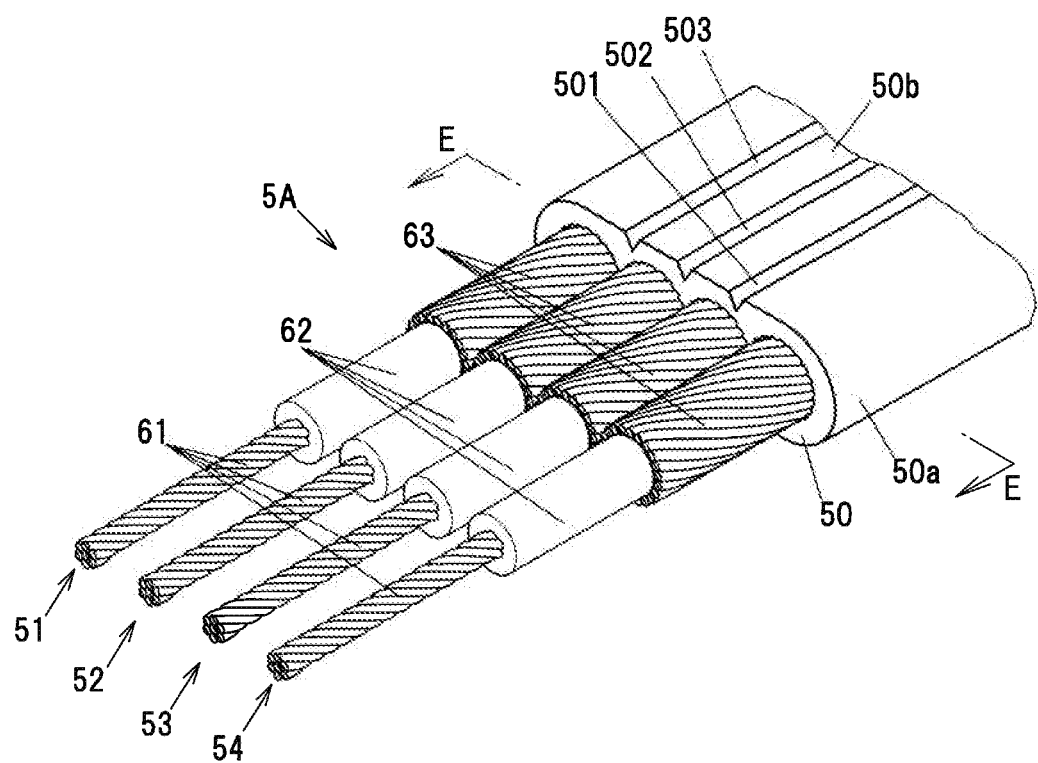
FIG. 7A is a perspective view showing an end in a longitudinal direction of a multi-core cable according to the second embodiment of the present invention.
Figure 7B:
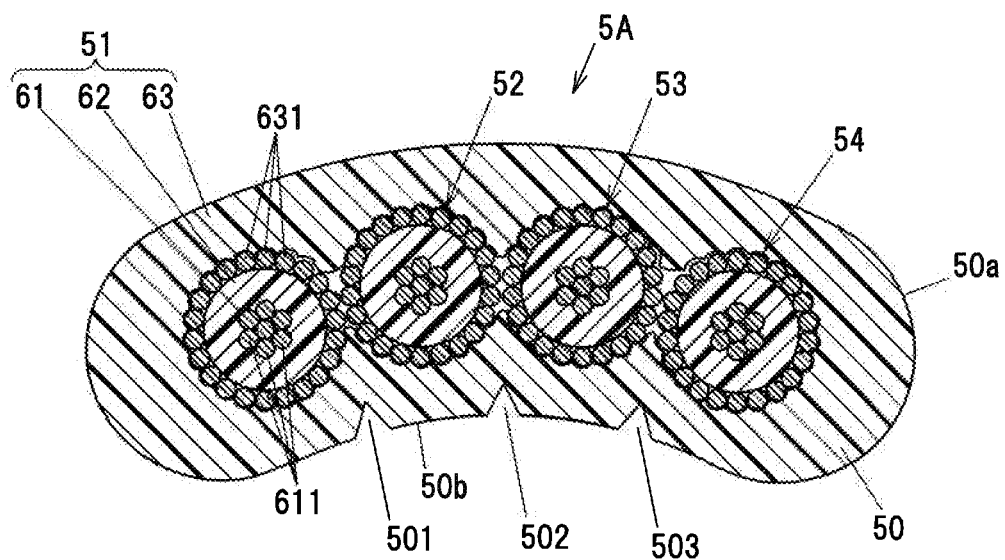
FIG. 7B is a cross-sectional view showing a cross-section perpendicular to a longitudinal direction of the multi-core cable according to the second embodiment when being elastically deformed in a circular-arc shape.

Next, referring to FIGS. 7A and 7B, a multi-core cable 5A according to the second embodiment of the present invention will be explained. The multi-core cable 5A has a configuration similar to the multi-core cable 5 according to the first embodiment except an indicator for indicating a front or back of the multi-core cable 5A on the covering member 50. In FIGS. 7A, 7B, the same reference signs as in FIGS. 3A, 3B will be assigned to the elements similar to the element in the multi-core cable 5 according to the first embodiment, and redundant explanations will be omitted. The same is applied in the third and fourth embodiments to be described below.

FIG. 7A is a perspective view showing an end in a longitudinal direction of the multi-core cable 5A according to the second embodiment of the present invention. FIG. 7B is a cross-sectional view showing a cross-section perpendicular to a longitudinal direction of the multi-core cable 5A according to the second embodiment when being elastically deformed in a circular-arc shape.

In the covering member 50 of the multi-core cable 5A, an indicator for indicating a front or back of the multi-core cable 5A is provided at one plane 50b in a direction perpendicular to the longitudinal direction of the multi-core cable 5A and the alignment direction of the first to fourth coaxial cables 51 to 54 in an outer surface 50a. In the present embodiment, as an example, the indicator is formed of first to third grooves 501 to 503 extending along the longitudinal direction of the multi-core cable 5A. In the alignment direction of the first to fourth coaxial cable 51 to 54, the first groove 501 is formed between the first coaxial cable 51 and the second coaxial cable 52, the second groove 502 is formed between the second coaxial cable 52 and the third coaxial cable 53, and the third groove 503 is formed between the third coaxial cable 53 and the fourth coaxial cable 54. The first to fourth coaxial cables 51 to 54 may be formed by utilizing e.g., a shape of a die to be used in extrusion molding of the covering member 50.

According to the present embodiment, in addition to the effect of the first embodiment, it is possible to connect the multi-core cable 5 to the substrate 4 without mistaking the two sides (front and back) of the multi-core cable 5A at the step of connection. Further, since the first to third grooves 501 to 503 are formed between respective ones of the first to fourth coaxial cables 51 to 54, groove depths thereof can be increased and the multi-core cable 5 can be connected to the substrate 4 without mistaking the two sides, even though the width of the multi-core cable 5A is narrow, for example. Further, the multi-core cable 5A can be easily deformed into a circular-arc shape as shown in FIG. 7B, so that the multi-core cable 5A can be easily arranged between the insertion tube 22 and the tube 23 as shown in FIG. 4, for example.

It should be noted that the indicator is not limited to the first to third grooves 501 to 503, and the indicator may be composed of a single groove. Further, the indicator is not limited to the groove, and the indicator may be formed by e.g., applying a coating (a paint) or partially changing a color of the resin to be extruded.

Third Embodiment

Figure 8:
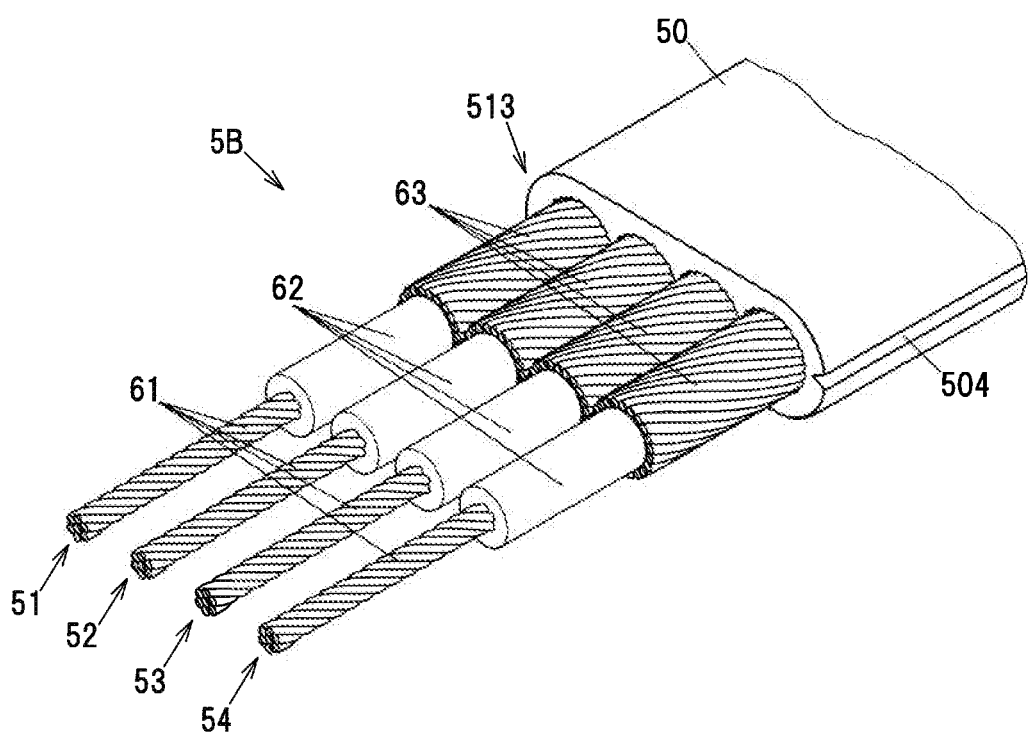
FIG. 8 is a perspective view showing an end in a longitudinal direction of the multi-core cable according to the third embodiment of the present invention.

Next, referring to FIG. 8, a multi-core cable 5B according to the third embodiment of the present invention will be explained. FIG. 8 is a perspective view showing an end of the multi-core cable 5B. In the multi-core cable 5B, a groove-shaped notch is formed at an outer surface 50a of the covering member 50 at both ends in the alignment direction of the first to fourth coaxial cables 51 to 54 along the longitudinal direction of the multi-core cable 5B. The notch 504 serves as a sign for indicating the direction of the two sides (the front and back) of the multi-core cable 5B, for example, when connecting the multi-core cable 5B to the substrate 4. Further, when the terminal processing of the multi-core cable 5B is manually performed, the terminal processing can be performed easily by sliding an edge of a cutting tool along the notch 504 to cut and open the covering member 50.

Fourth Embodiment

Figure 9A:
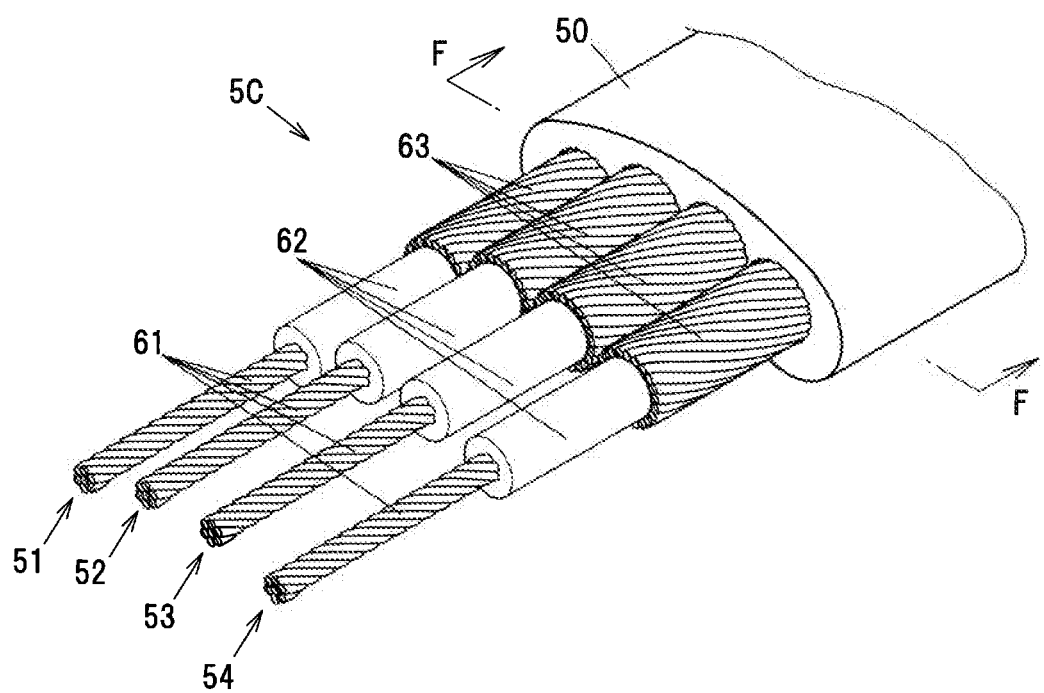
FIG. 9A is a perspective view showing an end in a longitudinal direction of the multi-core cable according to the fourth embodiment of the present invention.
Figure 9B:
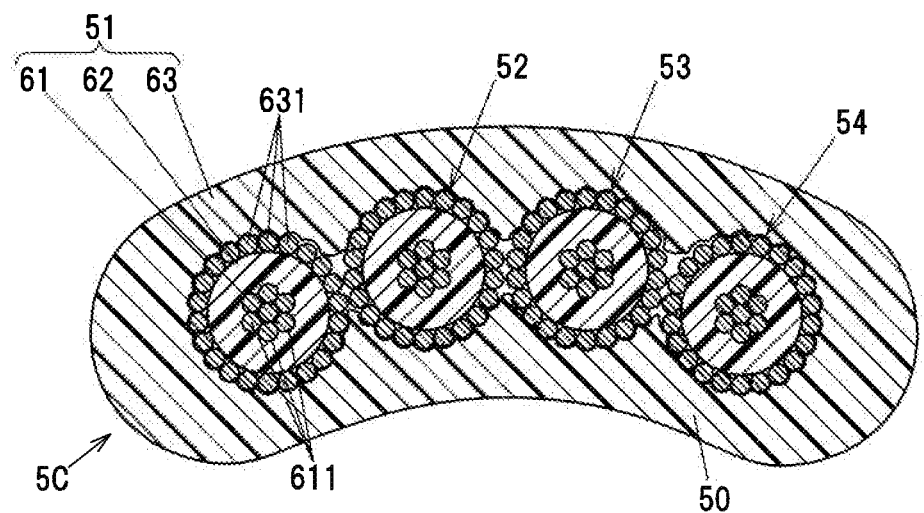
FIG. 9B is a cross-sectional view showing a cross-section perpendicular to a longitudinal direction of the multi-core cable according to the fourth embodiment.

Next, referring to FIGS. 9A and 9B, a multi-core cable 5C according to the fourth embodiment of the present invention will be explained. FIG. 9A is a perspective view showing an end in a longitudinal direction of the multi-core cable 5C according to the fourth embodiment of the present invention. FIG. 9B is a cross-sectional view showing a cross-section perpendicular to a longitudinal direction of the multi-core cable 5C cut along a line F-F according to the fourth embodiment. In the first embodiment, the case where the multi-core cable 5 is arranged between the insertion tube 22 and the tube 23 with being deformed to have a circular-arc cross-section is explained. In the multi-core cable 5C according to the present embodiment, the covering member 50 has a circular-arc shape in a cross-section perpendicular to the longitudinal direction of the first to fourth coaxial cables 51 to 54, in its original state to which no external force is applied. Hereby, even if the multi-core cable 5C is not elastically deformed by applying the external force, the multi-core cable 5C can be easily arranged between the insertion tube 22 and the tube 23 as shown in FIG. 4, for example.

Summary of Embodiments

Next, the technical concept grasped from the above-described embodiment is described with reference to the signs or the like in the embodiment. However, each sign or the like in the following description is not limited to a member or the like specifically showing the elements in the following claims in the embodiment.

[1] A multi-core cable (5, 5A, 5B, 5C), comprising:
a plurality of coaxial cables (51 to 54) being arranged in parallel with each other; and
a covering member (50) comprising a synthetic resin and collectively covering the plurality of coaxial cables (51 to 54), wherein each of the plurality of coaxial cables (51 to 54) comprises a center conductor (61), an insulator (62) covering an outer periphery of the center conductor (61), and an outer conductor (63) comprising a metal and covering an outer periphery of the insulator (62), wherein the covering member (50) is configured to hold the plurality of coaxial cables (51 to 54) in such a manner that the plurality of coaxial cables (51 to 54) are aligned side by side along a direction perpendicular to a longitudinal direction of the plurality of coaxial cables (51 to 54), wherein at least a part of respective outer conductors (63) of the plurality of the coaxial cables (51 to 54) contacts the covering member (50).

[2] The multi-core cable (5, 5A, 5B, 5C) according to [1], wherein a gap (S1 to S3) is formed between the covering member (50) and at least a part of an outer periphery (63) of the outer conductor (63) in a cross-section perpendicular to the longitudinal direction of the plurality of coaxial cables (51 to 54).

[3] The multi-core cable (5, 5A, 5B, 5C) according to [1] or [2], wherein at least parts of the respective outer conductors (63) of the plurality of coaxial cables (51 to 54) contact each other in a region covered with the covering member (50).

[4] The multi-core cable according (5A) to any one of [1] to [3], wherein an indicator (501 to 503) for indicating a front or back is provided at one plane (50b) in a direction perpendicular to the longitudinal direction of the plurality of coaxial cables (51 to 54) and an alignment direction of the plurality of coaxial cables (51 to 54) in an outer surface (50a) of the covering member (50).

[5] The multi-core cable (5A) according to [4], wherein the indicator (501 to 503) comprises a groove provided at a position corresponding to a space between the plurality of coaxial cables (51 to 54) along the longitudinal direction.

[6] The multi-core cable (5B) according to any one of [1] to [5], wherein the covering member (50) further comprises a notch (504) provided at an end in an alignment direction of the plurality of coaxial cables (51 to 54) along the longitudinal direction.

[7] The multi-core cable (5C) according to any one of [1] to [6], wherein the covering member (50) comprises a circular-arc shape in a cross-section perpendicular to the longitudinal direction of the plurality of the coaxial cables (51 to 54) in an original state to which no external force is applied.

[8] A signal transmission path (10), comprising:
the multi-core cable (5, 5A, 5B, 5C) according to any one of [1] to [7]; and
a substrate (4) comprising a plurality of wires (41, 42, 43, 44) including pads (411, 421, 431, 441) configured to be connected to the center conductors (61) of the plurality of coaxial cables (51 to 54),
wherein a pitch (P1) between the center conductors (61) is equal to a pitch (P2) between the pads (411, 421, 431, 441) of the substrate (4) in an alignment direction of the plurality of coaxial cables (51 to 54).

Although the embodiments of the invention have been described, the invention according to claims is not to be limited to the embodiments. Further, please note that all combinations of the features described in the embodiments are not necessary to solve the problem of the invention.

The various kinds of modifications can be implemented without departing from the gist of the invention. For example, although the cases where each of the multi-core cables 5, 5A, 5B, 5C comprises the first to fourth coaxial cables 51 to 54 are explained in the above embodiments, the number of the coaxial cables is not limited to four (4). For example, the number of the coaxial cables may be two or three (2 or 3), or five (5) or more. Further, the electric wires other than the coaxial cables may be collectively covered together with the plurality of coaxial cables by the covering member 50.

Further, when each of the multi-core cables 5, 5A, 5B, 5C is used for the endoscope 2, the number of the coaxial cables is preferably three to six (3 to 6). For transmitting the image data taken by the imaging element 333, at least three (3) coaxial cables are required. Further, when a light source such as LED for irradiating the light to the imaging target is arranged in the camera head 3, an additional coaxial cable for operating the light source is needed.

Further, although the cases where the tube 23 is used for supplying liquid such as physiological saline solution are explained in the above embodiments, the present invention is not limited thereto. For example, the tube 23 may be configured to accommodate a therapeutic instrument such as a clamp for treating a lesion. Further, a plurality of tubes may be arranged in the insertion tube 22, and one of the tubes may be used for supplying liquid such as physiological saline solution while the other tubes may be used for accommodating therapeutic instruments.

Furthermore, although the cases where the multi-core cable 5 is applied to the endoscope 2 are explained in the above embodiments, the application use of the present invention is not limited thereto, and the present invention can be applied to a multi-core cable for various purposes. For example, the present invention can be applied to a multi-core cable arranged in a catheter tube of a catheter for diagnostic imaging or a catheter balloon for vasodilation.

What is claimed is:
1. A multi-core cable, comprising:
a plurality of coaxial cables being arranged in parallel with each other; and
a covering member comprising a synthetic resin and collectively covering the plurality of coaxial cables,
wherein each of the plurality of coaxial cables comprises a center conductor, an insulator covering an outer periphery of the center conductor, and an outer conductor comprising a metal and covering an outer periphery of the insulator,
wherein the covering member is configured to hold the plurality of coaxial cables in such a manner that the plurality of coaxial cables are aligned side by side along a direction perpendicular to a longitudinal direction of the plurality of coaxial cables,
wherein at least a part of respective outer conductors of the plurality of coaxial cables contacts the covering member,
wherein a gap is formed between the covering member and at least a part of an outer periphery of the outer conductor in a cross-section perpendicular to the longitudinal direction of the plurality of coaxial cables, and
wherein the gap comprises a space in which the covering member enters between the plurality of coaxial cables.

2. The multi-core cable according to claim 1, wherein at least parts of the respective outer conductors of the plurality of coaxial cables contact each other in a region covered with the covering member.

3. The multi-core cable according to claim 1, wherein an indicator for indicating a front or back is provided at one plane in a direction perpendicular to the longitudinal direction of the plurality of coaxial cables and an alignment direction of the plurality of coaxial cables in an outer surface of the covering member.

4. The multi-core cable according to claim 3, wherein the indicator comprises a groove provided at a position corresponding to a space between the plurality of coaxial cables along the longitudinal direction.

5. The multi-core cable according to claim 4, wherein the outer conductor is configured by laterally winding a plurality of wires.

6. The multi-core cable according to claim 5, wherein the covering member enters into a space between adjacent wires of the plurality of wires.

7. The multi-core cable according to claim 5, wherein a space is formed between the adjacent wires of the plurality of wires and the covering member.

8. The multi-core cable according to claim 4, wherein the covering member enters into the gap between the plurality of coaxial cables.

9. The multi-core cable according to claim 3, wherein the covering member enters into a space between adjacent wires forming the outer conductor.

10. The multi-core cable according to claim 3, wherein a space is formed between adjacent wires forming the outer conductor and the covering member.

11. The multi-core cable according to claim 3, wherein the covering member enters into the gap between the plurality of coaxial cables.

12. The multi-core cable according to claim 1, wherein the covering member further comprises a notch at an end in an alignment direction of the plurality of coaxial cables along the longitudinal direction.

13. The multi-core cable according to claim 1, wherein the covering member comprises a circular-arc shape in a cross-section perpendicular to the longitudinal direction of the plurality of the coaxial cables in an original state to which no external force is applied.

14. A signal transmission path, comprising:
the multi-core cable according to claim 1; and
a substrate comprising a plurality of wires including pads configured to be connected to the center conductors of the plurality of coaxial cables,
wherein a pitch between the center conductors is equal to a pitch between the pads of the substrate in an alignment direction of the plurality of coaxial cables.

15. The multi-core cable according to claim 1, wherein the outer conductor is configured by laterally winding a plurality of wires.

16. The multi-core cable according to claim 15, wherein the covering member enters into a space between adjacent wires of the plurality of wires.

17. The multi-core cable according to claim 15, wherein a space is formed between adjacent wires of the plurality of wires and the covering member.

18. The multi-core cable according to claim 1, wherein at least parts of the respective outer conductors of the plurality of coaxial cables directly contact each other in a region covered with the covering member.

19. The multi-core cable according to claim 1, wherein at least a part of respective outer conductors of the plurality of coaxial cables directly contacts the covering member.

20. The multi-core cable according to claim 1, wherein the gap comprises the space in which the covering member enters between adjacent coaxial cables of the plurality of coaxial cables.

* * * * *